US008133691B2

(12) United States Patent
Ponniah et al.

(10) Patent No.: US 8,133,691 B2
(45) Date of Patent: Mar. 13, 2012

(54) STABLE QUANTITATION AND DETECTION OF IMMUNE RESPONSE LEVELS WITH NON-ZERO BACKGROUND PEPTIDES

(75) Inventors: Sathibalan Ponniah, Columbia, MD (US); George E. Peoples, Fulton, MD (US); Catherine E. Storrer, Columbia, MD (US); Michael Flora, Mt. Airy, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 702 days.

(21) Appl. No.: 11/994,794

(22) PCT Filed: Jul. 5, 2006

(86) PCT No.: PCT/US2006/025982
§ 371 (c)(1),
(2), (4) Date: Jul. 15, 2008

(87) PCT Pub. No.: WO2007/008488
PCT Pub. Date: Jan. 18, 2007

(65) Prior Publication Data
US 2008/0300203 A1   Dec. 4, 2008

Related U.S. Application Data

(60) Provisional application No. 60/696,508, filed on Jul. 6, 2005.

(51) Int. Cl.
*G01N 33/00* (2006.01)
*G01N 33/543* (2006.01)
*A61K 38/04* (2006.01)

(52) U.S. Cl. ........ 435/7.24; 435/7.1; 435/373; 435/375; 436/518; 436/523; 436/526; 436/528; 436/529; 436/177; 530/328

(58) Field of Classification Search ............... 435/7.1, 435/7.2, 7.24, 383, 373, 375; 436/518, 523, 436/524–535, 10, 177; 530/300, 326, 327, 530/328
See application file for complete search history.

(56) References Cited

U.S. PATENT DOCUMENTS

| | | | |
|---|---|---|---|
| 5,550,214 A | 8/1996 | Eberlein et al. | |
| 6,037,135 A | 3/2000 | Kubo et al. | |
| 6,110,380 A | 8/2000 | Barbera-Guillem | |
| 6,126,835 A | 10/2000 | Barbera-Guillem | |
| 6,150,122 A * | 11/2000 | Lee et al. | 435/7.24 |
| 6,211,342 B1 | 4/2001 | Hirsch et al. | |
| 6,514,942 B1 | 2/2003 | Ioannides et al. | |
| 6,815,171 B2 | 11/2004 | Burrows et al. | |
| 7,521,197 B2 * | 4/2009 | Savage | 435/7.24 |
| 2003/0185822 A1 * | 10/2003 | Grey et al. | 424/143.1 |
| 2003/0223994 A1 | 12/2003 | Hoogenboom et al. | |
| 2004/0157273 A1 | 8/2004 | Sidney et al. | |
| 2005/0287631 A1 * | 12/2005 | Kroenke et al. | 435/69.1 |

FOREIGN PATENT DOCUMENTS

| | | |
|---|---|---|
| WO | WO-97/34621 | 9/1997 |
| WO | 02072766 | 9/2002 |
| WO | 2005012350 | 2/2005 |

OTHER PUBLICATIONS

Parkhurst M. R. et al., "Immunization of Patients with hTERT:540-548 Peptide Induces Peptide-Reactive T Lymphocytes That do not Recognize Tumors Endogenously Expressing Telomerase", Clinical Cancer Research, vol. 10, Jul. 15, 2004, pp. 4688-4698.

* cited by examiner

*Primary Examiner* — Gail R Gabel
(74) *Attorney, Agent, or Firm* — MH2 Technology Law Group LLP (57) ABSTRACT

The invention relates to a kit comprising MHC Class I and Class II HLA-coated beads containing specific antigenic peptides for binding to antigen-specific T cells and the appropriate negative control peptides. Also provided are methods for making the coated beads and methods for use. The application of these beads go to the stimulation of peripheral blood cell populations and in vitro-stimulated culture for the elicitation of functional activities such as cell activation and signaling, cytokine secretion, proliferation and cytotoxicity activity.

20 Claims, 1 Drawing Sheet

FIG. 1B

FIG. 1A

SEQUENCE LISTING

<160> NUMBER OF SEQ ID NOS: 5

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ile Ala Trp Ala Arg Thr Glu Leu
 1               5

-continued

```
<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Ile Trp Thr His Ser Thr Lys Val
 1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Ile Trp Thr His Ser Tyr Lys Val
 1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ile or Leu

<400> SEQUENCE: 4

Xaa Ile Leu Ala Lys Phe Leu His Trp Leu
 1               5                  10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu Ile Leu Ala Lys Phe Leu His Trp Leu
 1               5                  10
```

STABLE QUANTITATION AND DETECTION OF IMMUNE RESPONSE LEVELS WITH NON-ZERO BACKGROUND PEPTIDES

REFERENCE TO RELATED APPLICATIONS

This application claims priority to U.S. Provisional Application No. 60/696,508 filed Jul. 6, 2005 entitled "Stable Quantitation and Detection of Immune Response Levels with Non-Zero Background Peptides," the entirety of which is hereby incorporated by reference.

RIGHTS IN THE INVENTION

This invention was made, in part, with support for the United States government and the United States government may have an interest in this invention.

BACKGROUND

1. Field of the Invention

This invention is directed to short peptides that, when associated with MHC molecules for presentation to T cells, produces a stable, non-zero background, immune response from the T cells. The invention is also directed to complexes comprising the peptides and MHC molecules, and complexes coupled with chromatography and other beads. Further, the invention is directed to methods of quantitating immunological assays with peptides and beads of the invention, and methods of identifying new peptides that produce a stable, non-zero background immune response.

2. Description of the Background

One of the critical aspects for the successful evaluation of clinical trials for the immunotherapy of cancer is the ability to monitor critical parameters of the ongoing in vivo immune responses elicited by the vaccine. The classical assays for the immunological monitoring of individuals receiving peptide vaccines have consisted predominantly of in vitro cell culture-based assays such as proliferation, cytokine secretion into supernatants (ELISA), cytotoxicity and antibody responses. The in vitro manipulation of the patient's peripheral blood cells in these assays and the 'real-time distance' from acquisition of the blood sample prior to gaining any data have made it difficult to appreciate valuable and directly relevant insights about the vaccine and the resulting immune response. Newly developed technology along with improved reagents and protocols are now available for a more rapid and less manipulated assessment of immunological responses.

MHC molecules are classified as either Class I or Class II molecules. Class II MHC molecules are expressed primarily on cells such as B lymphocytes, macrophages, etc. Class II MHC molecules are recognized by CD4-helper T lymphocytes and induce proliferation (growth or reproduction of similar cells) of helper T lymphocytes and amplification of the immune response to the particular immunogenic peptide that is displayed. Class I MHC molecules are expressed on almost all nucleated cells and are recognized by CD8 cytotoxic T lymphocytes (CTLs), which then induce lysis of the 'foreign' antigen-bearing cells. CTLs are particularly important in tumor rejection and in fighting viral infections. The CTL recognizes the antigen in the form of a peptide fragment bound to the MHC Class I molecule, rather than the intact foreign antigen itself. The antigen is normally derived from endogenously synthesized proteins within the cell that are then degraded into small peptide fragments in the cytoplasm.

Immunogenic peptides having binding motifs for MHC Class I molecules are typically between about 8 and about 11 amino acid residues and comprise conserved residues involved in binding proteins encoded by the appropriate MHC allele. Epitopes on a number of potential target proteins can be identified using conserved 'anchor' amino acids. Examples of antigens with well defined anchor amino acid residues include peptides from prostate specific antigen (PSA), hepatitis B core and surface antigens (HBVc, HBVs), hepatitis C antigens, malignant melanoma antigen (MAGE-1), Epstein-Barr virus antigens, human immunodeficiency type-1 virus (HIV1), and papilloma virus antigens. The peptides are known to be useful in pharmaceutical compositions for both in vivo and ex vivo therapeutic and diagnostic applications (see U.S. Pat. No. 6,037,135).

The most established and acclaimed of the new reagents for the detection and measurement of immunological responses are the MHC dimer and tetramer molecules that allow for the specific detection and quantification of antigen-specific T lymphocytes. From an immune response point of view, the enumeration of antigen-specific T cells by dimer and tetramer analysis by itself is unable to provide any information on the functional immunological activity associated with these cells. However, when used in combination with improved intracellular staining protocols and the rapid stimulation of peripheral blood cells with minimal manipulation, dimer and tetramer analysis has the potential to allow for the detection of cytokine secretion within these cells.

There are generally two methods for the detection of cytokine secretion by antigen-specific T cells. The first is the intracellular cytokine (ICC) secretion by flow cytometry that has the potential to provide both a phenotypic and functional characterization of the cytokine response. A limitation of this method is that it is dependent on the period and conditions of stimulation, and has a rather 'restrictive' narrow window of time that is assumed and allowed for the optimal detection of the peak cytokine secretion activity during the staining process.

The second method is where cells are stimulated in culture and the cytokine secretion monitored over a longer period of time by the ELISPOT method, allowing for an extended period of secretion and capture of the secreted cytokine, thereby resulting in enhanced detection of functional activity. Advances in optical instrumentation and digital image analysis software offer promise that a certain level of standardization can be achieved between laboratories using the ELISPOT assay for enumerating cytokine secreting cells in response to specific antigenic peptide stimulation.

Based upon their findings at a recent workshop, the Society of Biological Therapy (SBT) has recommended that future clinical trials should strive to utilize direct methods for the phenotypic (such as tetramer or dimer analysis) and functional analysis of immune cells (such as ICC and ELISPOT) in the immunological monitoring of peptide vaccine clinical trials.

The SBT downgraded the other assays such as the proliferation assay and the cytotoxicity assay largely because of the prolonged in vitro manipulations and culture conditions. However, these assays can also have the potential of being important and informative if the number of in vitro manipulations can be kept to a minimum and stimulatory reagents of manageable consistency can be made available.

It is desirable, therefore, to provide an improved method for detecting and accurately measuring functional activities associated with immune cells during an immune response including use of the proliferation assay and the cytotoxicity assay for immunological monitoring of peptide vaccines.

There are various methods available to isolate or separate biological molecules such as cells, antibodies, antigens, proteins, carbohydrates, nucleic acids, and the like. Magnetic separation techniques typically involve the application of a magnetic field to separate ferromagnetic particles contained within a fluid medium. Magnetic separation of one or more targeted molecules present in a solution comprising a mixed population of molecules is well known and the necessary materials are all commercially available (see U.S. Pat. Nos. 6,110,380 and 6,126,835). More particularly, the separation of target biological molecules was conducted using magnetic particles and a magnetic separation device. However, that magnetic separation was limited to use of a fluid containing a mixed population of biological molecules and magnetic particles coated with a ligand (magnetic separation reagent) having sufficient binding specificity and affinity for the target biological molecule.

SUMMARY

As embodied and broadly described herein, the invention is directed to short peptides that, when associated with MHC molecules for presentation to T cells, produces a stable, non-zero background, immune response.

Conventional procedures for identifying peptides from isolated MHC Class I molecules (e.g. see U.S. Pat. No. 6,037,135), do not disclose methods for identifying peptides for negative control runs for use with immunological monitoring of immune response assays. The present invention overcomes the problems and disadvantages associated with current methods of stimulating cells in culture for detection of cytokine secretion. The present invention provides new tools and methods for using HLA coated beads (e.g. DYNAL beads) in immunological assays and identifying the appropriate negative peptides for monitoring background or 'deviant' stimulatory responses. In its particular embodiments, the present invention provides methods for ensuring consistency in the concentration, quantity and/or quality of the levels of the antigenic peptide being taken up, processed and presented in the context of the HLA molecules. The invention provides an artificial 'stimulatory cell' for stimulating the antigen-specific T cells and circumventing the inconsistencies associated with the "unknown" levels and/or quality of peptide presentation seen with the usual antigen-presenting cells. The invention also provides a process of identifying three peptides that can be used for monitoring background or 'deviant' stimulatory responses and the process of pre-folding two of these peptides within the HLA molecules to generate two species of negative-control beads to be tested along with their antigen-specific beads in ex vivo ELISPOT assays.

The present invention is valuable for monitoring vaccine trials for a wide range of peptides. The present invention can be used as a kit or reagent so that a consistent product is being used by different investigators, whereby the results can be accordingly compared between separate laboratories. The ex vivo nature of the assay also provides extended use in diagnosis.

The present invention also presents a novel method of magnetic separation. Conventional means were limited to using ligands for binding to a target biological molecule for separation. In the present invention, beads are coated with MHC Class I HLA containing specific antigenic peptides or MHC Class II HLA containing specific antigenic peptides for binding the beads to antigen-specific T cells for magnetic separation. The beads can also be coated with MHC Class I H-2 and Class II I-A/I-E molecules for murine testing and MAMU MHC molecules for primate studies.

Other embodiments and advantages of the invention are set forth in part in the description, which follows, and in part, may be obvious from this description, or may be learned from the practice of the invention.

DESCRIPTION OF THE FIGURE

FIG. 1 depicts the process of immunotherapy and generation of the immune response according to one embodiment of the invention.

DESCRIPTION OF THE INVENTION

Definitions

The term "anchor amino acid" is used herein, for purposes of the specification and claims, to mean an amino acid (e.g. modified or unmodified) of a short peptide whose position in that peptide provides optimal binding affinity to a near-by amino acid of an MHC molecule preferably within the binding cleft of the MHC molecule, whose affinity is necessary for the proper association of the peptide with the MHC molecule for presentation to a T cell in the generation of an immune response.

The term "antigen" is used herein, for purposes of the specification and claims, to mean a substance that is capable of inducing an immune response.

The term "beads" is used herein, for purposes of the specification and the claims, to mean chromatography matrix materials including, but not limited to: ionic and non-ionic materials, anion and cation exchange materials, affinity materials, size exclusion materials, Sepharose®, Sephadex®, agarose, cellulose, adsorption/partition material, activated matrices, resins, nanoparticle structures and complexes from these materials, and combinations thereof.

The term "biological molecule" is used herein, for purposes of the specification and claims, to mean a substance derived or obtained from a biological materials including, but not limited to: eukaryotic and prokaryotic cells; sub cellular structures such as mitochondria, membranes and other cell parts; molecules such as peptides, polypeptides, proteins, carbohydrates, lipids, nucleic acids, fatty acids and complex molecules including glycoproteins, lipoproteins, antibodies, cell factors, aptamers, and pharmaceutical compounds and drugs, and combinations of any of the preceding.

The term "C-terminus amino acid" is used herein, for purposes of the specification and claims, to mean the amino acid whose amino group participates in the formation of the peptide bond, but still has a free carboxyl group. In a linear peptide, the C-terminus is conventionally written to the right.

The term "cytotoxicity" is used herein, for purposes of the specification and claims, to mean the degree to which a substance is able to induce the death, lysis or otherwise destruction of cells.

The term "ELISA" is used herein, for purposes of the specification and claims, to mean the abbreviation for enzyme linked immunosorbent assay, which is a serological assay in which bound antigen or antibody is detected by a linked enzyme that converts a substrate to a detectable (e.g., colored) product.

The term "ELISPOT" is used herein, for purposes of the specification and claims, to mean an adaptation of ELISA in which cells are placed over antibodies or antigens attached to a plastic surface. The antigen or antibody traps the cells' secreted products, which can then be detected by using an enzyme-coupled antibody that cleaves a preferably colorless substrate to make a localized colored spot.

The term "epitope" is used herein, for purposes of the specification and claims, to mean a site on an antigen recognized by antibody. Epitopes are also called antigenic determinants.

The term "HLA" is used herein, for purposes of the specification and claims, to mean human leukocyte antigen.

The term "H-2" is used herein, for purposes of the specification and claims, to mean the major histocompatibility complex situated on chromosome 17 of the mouse, containing subregions K, I and D.

The term "IL" is used herein, for purposes of the specification and claims, to mean interleukin, which is a type of cytokine produced by leukocytes that influences a variety of cells.

The term "immune response" is used herein, for purposes of the specification and claims, to mean the reaction of the immune system to an antigen.

The term "MHC" is used herein, for purposes of the specification and claims, to mean major histocompatibility complex. The MHC is a gene cluster of all or at least most mammals (e.g. humans, primates, mice) that controls antigen-presentation in the immune response. In humans, class I molecules are designated HLA-A, B and C; class II molecules are designated HLA-DP, DQ and DR; and class III molecules are the non classical MHC molecules. The murine MHC molecules are designated H-2.

When referring to antigens of the invention, the term "non-zero background" is used herein, for purposes of the specification and claims, to mean a measure of the response produced from an in vitro immune assay that represents a minimal antigenic activity.

The term "N-terminus amino acid" is used herein, for purposes of the specification and claims, to mean the amino acid whose carboxyl group participates in the formation of the peptide bond, but has a free amino group. In a linear peptide, the N terminus is conventionally written to the left.

When referring to an immune response, the term "stable" is used herein, for purposes of the specification and claims, to mean an immune response that is consistent and reproducible in relation to a test antigen.

PREFERRED EMBODIMENTS

The immune response is one of the most well known and well studied molecular mechanisms of the immune system. In spite of this thorough understanding, immune response profiles vary greatly between laboratories and even within the same laboratory when assaying an immune response for the same antigen.

It has been surprisingly discovered that the immune response of a particular system could be standardized, not by presenting controls of MHC molecules without associated antigen, but by presenting MHC molecules in association with an antigen that produces a stable, but non-zero background response. Only such antigens consistently and reproducibly produce an immune response that represents only background activity, and not an aberration from artifacts of the particular system. This non-zero background activity can be used as a control or baseline from which the antigenicity of a test antigen can be sensitively, accurately and quantitatively measured.

One embodiment of the invention comprises short peptides that produce a stable, non-zero-background response in an immunological assay. These short peptides of the invention may be of any size that allows for association with MHC molecules for presentation to a cell population to elicit an immune response. Peptides of the invention preferably contain a single peptide sequence from 6 to 36 amino acids in length, and preferably contain at least two anchor amino acids. Generally, the larger the sequence, the greater the number of anchor amino acids necessary for association with the appropriate MHC molecule for presentation. More preferably, the peptides are from 8 to 25 amino acids in length, with from 2 to 5 anchor amino acids. Even more preferably, sequences are from 10 to 20 amino acids, and contain from 2 to 4 anchor amino acids. Peptide sequences of 7, 9, 11, 12, 13, 14, 15, 16, 17, 18, 19, 21, 22, 23, 24, 26, 27, 28, 29, 30, 31, 32, 33, 34 and 35 amino acids are also contemplated, containing any of 1, 2, 3, 4, 5, 6, or more anchor amino acids. Although sequences will mostly contain naturally occurring amino acids, one or more (or all) non-naturally occurring, synthetic and/or modified amino acids may also comprise the peptide sequence of the invention. Amino acids may be modified or coupled with other molecules, provided the peptide is able to elicit some measure of an immune response. In a preferred embodiment of the invention, the short peptide has a sequence of 8 to 10 naturally occurring amino acids and contains two anchor amino acids, at least one at position 1, 2 or 3, and at least one other at position 7, 8, 9 or 10 (when counting from the N-terminus to the C-terminus of the peptide). Another preferred embodiment is a peptide of from 7 to 24 amino acids, with at least one anchor amino acid at any of positions 2-5 from the N-terminus, and at least one other anchor amino acids at any of positions 2-7 from the C-terminus. Other preferred locations of anchor amino acids along the peptide chain are between amino acid positions 12 and 17 (counting from the N-Terminus), with peptides of from 22 to 28 amino acids, and between amino acid positions 22 and 25, with peptides of from 30 to 36 amino acids.

Anchor amino acids can be identified for most any peptide by those skilled in the art. For example, U.S. Patent Application Publication No. 2004 0157273, which was published Aug. 12, 2004 (and is entirely incorporated by reference), provides methods whereby amino acids of a peptide sequence with a high affinity to MHC antigen can be identified. Coefficients of affinity can be determined for such peptides for use in the development of algorithms for the prediction of specific binding sites of a peptide.

Investigations of the crystal structure of the human MHC class I molecule, HLA-A2.1, show that a peptide binding groove is created by the folding of the alpha.1 and alpha.2 domains of the class I heavy chain (Bjorkman, et al., Nature 329:506 (1987)). Buus, et al., Science 242:1065 (1988), described a method for acid elution of bound peptides from MHC. Subsequently, Rammensee and his coworkers (Falk, et al., Nature 351:290 (1991)), developed an approach to characterize naturally processed peptides bound to class I molecules. Other investigators have successfully achieved direct amino acid sequencing of the more abundant peptides in various HPLC fractions by conventional automated sequencing of peptides eluted from class I molecules of the B type (Jardetzky, et al., Nature 353:326 (1991)) and of the A2.1 type by mass spectrometry (Hunt, et al., Science 225:1261 (1992)). A review of the characterization of naturally processed peptides in MHC Class I has been presented by Rotzschke & Falk (Rotzschke & Falk, Immunol. Today 12:447 (1991)). PCT publication WO 97/34621, incorporated herein by reference, describes peptides which have a binding affinity for A2.1 alleles. Sette, et al., Proc. Nat'l. Acad. Sci. USA 86:3296 (1989) showed that MHC allele specific motifs can predict MHC binding capacity. Schaeffer, et al., Proc. Nat'l. Acad. Sci. USA 86:4649 (1989), showed that MHC binding was related to immunogenicity. Others (De Bruijn, et al., Eur. J. Immunol., 21:2963-2970 (1991); Pamer, et al., 991

Nature 353:852-955 (1991)), provided preliminary evidence that class I binding amino acids can be applied to the identification of potential immunogenic peptides in animal models. The combined frequencies of these different alleles should be high enough to cover a large fraction or perhaps the majority of the human outbreed population. From these and other investigations, all well-known by those skilled in the art, the identity of amino acids bound to the groove, which in most cases is the high affinity binding site, of an MHC molecule can be determined. Most preferably, these are the anchor amino acids.

Another embodiment of the invention comprises a nucleic acid sequence that encodes a peptide of the invention. Such nucleic acids sequence may be used in expression systems to produce large quantities of peptides of the invention. Such expression systems may be prokaryotic or eukaryotic, or designed to express sequences containing one or more modified amino acids.

Another embodiment of the invention comprises peptides of the invention in association with MHC molecules. Association is most typically non-covalent, such as by hydrogen bonding, van der Waals forces, hydrophobic or hydrophilic interactions, or combination thereof. However, association may be made covalent using well known methods to covalently bind amino acids that are in close proximity to one another. Such methods include chemical treatment, radiation exposure or other well-known methods.

MHC molecules that may be used are preferably mammalian MHC molecules including, but not limited to, human, primate, murine, equine, porcine, feline, canine, ovine or sheep, caprine or goat, and even shark MHC molecules, and combinations thereof. MHC molecules of the invention include, but are not limited to, molecules classified as class I, II or III, HLA, H-2 and combinations thereof. Class I MHC molecules are expressed on almost all nucleated cells and are recognized by cytotoxic T lymphocytes (CTLs), which then destroy the antigen-bearing cells. Class II MHC molecules are expressed primarily on cells involved in initiating and sustaining immune responses, such as T lymphocytes, B lymphocytes, macrophages, etc. Class II MHC molecules are recognized by helper T lymphocytes and induce proliferation of helper T lymphocytes and amplification of the immune response to the particular immunogenic peptide that is displayed.

Figure 1A:
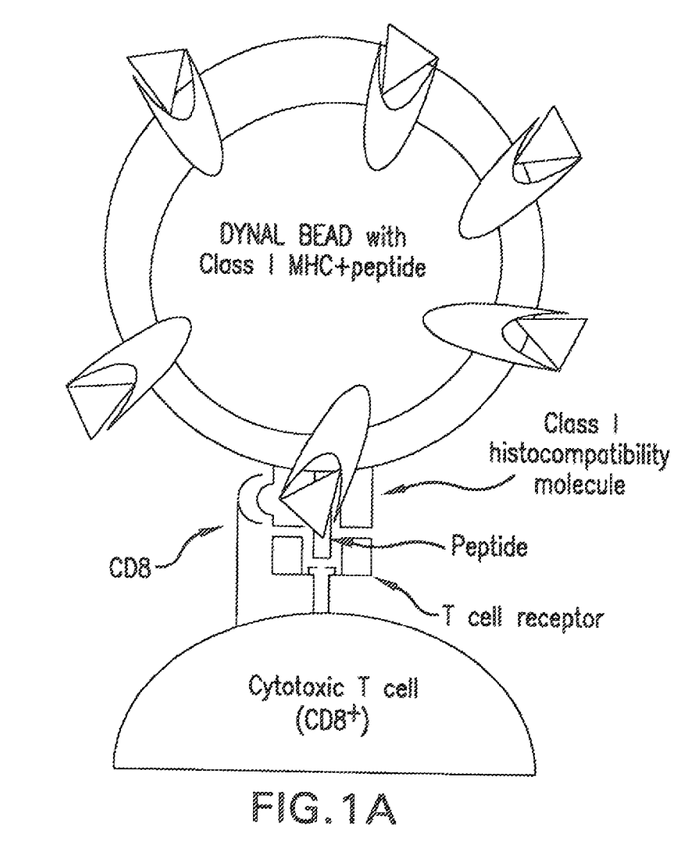
Figure 1B:
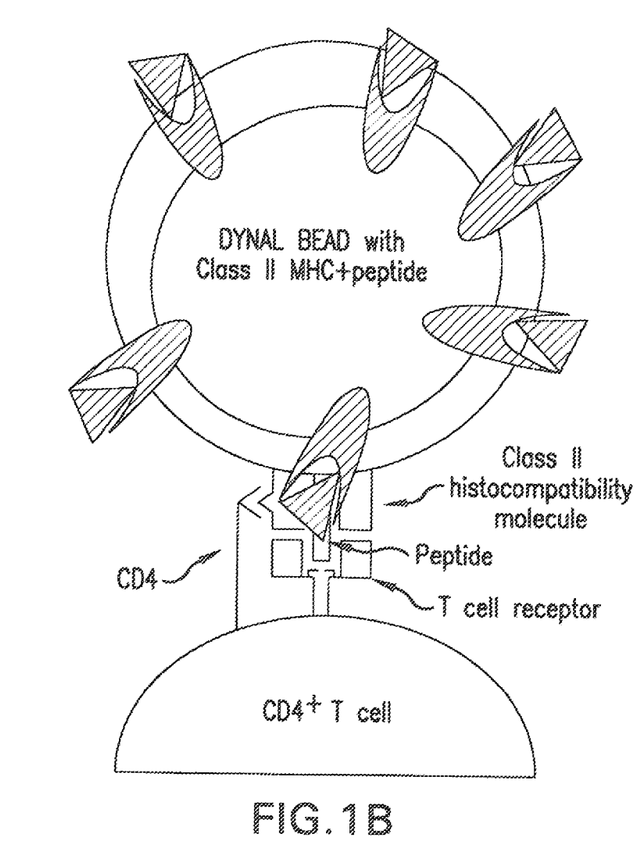

Another embodiment of the invention comprises peptides of the invention in association with MHC molecules, covalently or non-covalently coupled to a solid structure such as any of a variety of beads, such as chromatography media, and biological or chemical structures such as nanoparticles (see FIG. 1). Any type of conventional bead may be used, including, but not limited to, beads made of agarose, Sephadex®t, Sepharose®, affinity material, exchange material, biological materials such as those used for in vivo applications, and many other materials, all well-known to those skilled in the art. Beads preferably contain peptides prefolded within, for example, HLA molecules for binding the beads to antigen-specific T cells. The beads may be superparamagnetic, that is, they exhibit magnetic properties only when placed within a magnetic field and show no residual magnetism when removed from this field. For example, beads made from DYNAL Biotech have a polymer shell that protects the target from toxic exposure to iron. The true uniformity (CV<3%) of size, shape and surface area provides optimal accessibility and reaction kinetics, allowing for rapid and efficient binding. The true spherical shape and defined surface chemistry minimize chemical agglutination and non-specific binding. The specific characteristics of the many available bead types facilitate magnetic separation of a wide variety of targets. Advantages of these beads include unique batch-to-batch reproducibility, which secures the reproducibility and quality of results, magnetic separation is gentle and no column or centrifugations are necessary. Reproducibility is typically within 10%, preferably within 5%, and more preferably within 1% or 2%. Similar bead particles are also available as magnetic nanoparticles from BD Bioscience Pharmingen (BD IMag Particles). The smaller size characteristics of the IMag particles have the added advantage of being useful for the isolation and purification of cell populations that can then be moved or taken directly into downstream applications such as flow cytometry analysis without necessitating removal of the beads from the cells.

Another embodiment of the invention comprises kits containing beads of the invention. Such kits can be manufactured with preferred peptides associated with any of a variety of MHC molecules (e.g. human {HLA}, mouse {H-2}, primate {MAMU-MHC3}, etc.), and coupled with beads for use in in vitro or in vivo immunological assays. These kits may contain appropriate buffers and containers for direct, head-to-head comparison of a desired test peptide against the control peptide of the invention, which comes in the kit. By providing a common methodology, the exact degree of antigenicity, as compared to the control peptide, can be determined and compared with all other tests of that peptide, whether performed in other laboratories, or even in other assays that used the same peptide control.

Another embodiment of the invention comprises methods for quantitating the antigenicity of a test antigen by comparison against a peptide of the invention. Peptides are preferably associated with MHC molecules, and coupled with beads. The test peptide is also associated in a similar or identical manner with the same or a similar MHC molecule, and coupled with the same or a similar bead material. Methods involve performing an immunological assay, such as, but not limited to, an ELISPOT assay, an ELISA, and immune response assays that are well-known to those skilled in the art. The assay will determine the degree of antigenicity of the test peptide, which can be compared with the control peptide of the invention. The control peptide establishes a base-line of floor measurement from which an exact measure or quantitation of the antigenicity of the test peptide can be determined. Further, databases of the relative antigenicities of many different test peptides can be established by comparisons against one or a small number of control peptides.

Another embodiment of the invention comprises methods of screening for stable, non-zero background responsive antigens. Using immune response assays that are both well known and commercially available, one skill in the art can screen large numbers of antigens and, instead of screening for antigens that produce strong immunogenic reactions, identify those which produce a stable, non-zero background response according to the invention. Preferred antigens are peptide sequences, but such antigens may be simple or complex organic or inorganic chemicals, biological materials, or any combinations thereof.

In one specific embodiment, the invention comprises methods for making and using the MHC Class I HLA-coated beads in a magnetic system to extract T cells for subsequent applications such as expansion in culture, DNA extraction and analyses, and the like. Further, the present invention includes novel applications for the MHC Class I HLA-coated beads for use in stimulation of antigen-specific CD8 T cells leading to and resulting in biochemical responses and functional activities that can be detected by biochemical methods and procedures and immunological assays. The invention also includes other applications the beads may be used for when coated with other MHC molecules such as MHC Class II HLA molecules and non-classical MHC molecules.

One aspect for the successful investigations of diagnosis, monitoring and evaluation of clinical trials and vaccine studies for the immunotherapy of cancer, infectious diseases and autoimmunity is the ability to monitor critical parameters of the ongoing in vivo immune responses being elicited by the vaccine. The classical assays for the immunological monitoring of individuals receiving peptide vaccines consists predominantly of in vitro cell culture-based assays such as proliferation, cytokine secretion into supernatants (ELISA), cytotoxicity and antibody responses. These assays typically involve a number of preparatory steps to process the peripheral blood cells and in vitro manipulations that can take anywhere from 2 days to 2 weeks to obtain the results. Therefore, assays conducted by different laboratories are very often fraught with considerable variations and artifacts that can arise from the blood sample itself or from the technician performing the procedures of the assay. The occurrence of such problems in the task of immunological monitoring have made very it difficult to appreciate valuable scientific insights about the vaccines being tested and the resulting immune response. Therefore a more rapid and less manipulated assessment of immunological responses is very desirable for achieving advances in the field of vaccine development and treatment.

Currently there are two methods for the detection of cytokine secretion by antigen-specific T cells. The first is the intracellular cytokine (ICC) secretion by flow cytometry that has the potential to provide both a phenotypic and functional characterization of the cytokine response. The limitation of this method is that it is dependent on the strength of the antigenic stimulatory signal delivered to the T cell and the rather 'restrictive' narrow window of time that is assumed and allowed for the optimal detection of the peak cytokine secretion activity during the staining process.

The second method is where cells are stimulated in culture and the cytokine secretion monitored over a longer period of time by the ELISPOT method thereby allowing for an extended period of secretion and capture of the secreted cytokine. Advances in optical instrumentation and digital image analysis software offer promise that a certain level of standardization can be achieved between laboratories using the ELISPOT assay for enumerating cytokine secreting cells in response to specific antigenic peptide stimulation. In most cases, the peptide-specific stimulation of the T cells in the ELISPOT assay is achieved by antigen-presenting cells (APC) such as B cells, monocytes and dendritic cells that are already present as subpopulations of the peripheral mononuclear blood cells. As a means of increasing the numbers of APC available for the stimulation of the T cells, very often highly purified populations of the dendritic cells or monocytes can also be prepared and used for the antigenic stimulation of the entire population of the peripheral blood samples. In some cases the antigenic peptides is pulsed onto the APCs or mixed in with the culture during the stimulatory phase. This approach then requires for the antigenic peptide to be taken up and processed into the antigen-presenting machinery and loaded onto HLA molecules for eventual presentation on the cell surface to the T cell receptors of antigen-specific T cells. Despite the importance of this step, there is no method available for ensuring any level of consistency in the concentration and/or quantity and quality of the levels of the antigenic peptide being taken up, processed and making it to the final and crucial step, i.e., presented in the context of the HLA molecules at the cell surface. And since this is the initial step and probably the most important one in the chain of subsequent downstream culture stimulation conditions that follow, it is also the reason for the amount of variability seen in the immune responses in the subsequent monitoring assays. A weakness here results from the variation and inadequate presentation of peptide be it the quantity or quality of peptide that matters.

To enable the antigen to stimulate the antigen-specific T cells and circumvent the inconsistencies associated with the variable, "unknown" levels and/or quality of peptide presentation seen with the usual antigen-presenting cells, the present invention uses an artificial 'stimulatory cell'. This cell has a defined amount of HLA molecules folded around the specific peptide, all of which will potentially express and present the antigenic peptide of interest. An advantage of the HLA coated beads (such as those made by DYNAL or the IMag particles from BD Biosciences Pharmingen or other commercially available beads) is that they can be biochemically synthesized in large quantities and monitored by quality control processes for consistence and adequate levels of HLA with bound peptide to be presented on their surface. And since almost all of the HLA molecules will be presenting the peptide of interest, therefore the presence of several HLA molecules being available to engage one or more of the T cell receptors simultaneously ensure or generate strong stimulatory interactions and signaling events resulting in the elicitation of T cell responses to occur successfully and consistently. This aspect is also the reason that co-stimulatory signals and/or cytokines may not be needed. However, if necessary or desired, they can be also incorporated or bound to the beads at the same time or added to the culture.

The limitations of the HLA beads for use in such immunological assays would be the availability of appropriate negative peptides that can be used for monitoring background or 'deviant' stimulatory responses. The identification of such peptides can often be near impossible because of the intrinsic nature of the immune T cells whereby they are made to recognize the broadest variability of peptides. The present invention solves this problem. The present invention identifies peptides for this specific purpose.

Three peptides were identified from experiments which showed strong binding affinities for the MHC Class I molecules. Each peptide sequence is comprised of about 8-10 amino acids (numbered from the N-terminus) and contained at least two anchor amino acids. At least one anchor amino acid was located at position 1, 2, or 3, and at least one other was located at position 7, 8, or 9. These anchor amino acids are preferably charged, which may be either a positive or negative charge. For example, one peptide had a sequence of 9 amino acids with the anchor amino acids in positions 2 and 9.

The three identified peptides bound equally well to MHC as the control peptide and elicited a stable non-zero background response. Two of these peptides folded into HLA molecules, and bound to beads to generate two species of negative control beads that were tested along with the antigen-specific beads and native/plain peptide in ex vivo ELISPOT assays.

Experiments to develop and validate this idea for the utilization of these beads and the appropriate negative controls for the ELISPOT assay (IFN-γ, granzyme and perforin) support the present invention. Ex vivo stimulations for the generation of proliferation and cytotoxicity and cell activation functions and responses enhance the applicability of these beads to a wider utilization in both clinical and research studies.

Furthermore, the inclusion of measurements related to cell activation triggered by these beads such as the detection of signal transduction pathways and associated components and biochemical responses such as calcium mobilization and phosphorylation are useful for both basic research investigations and clinical studies in the healthy and disease conditions.

All of the approaches and applications described herein are also similarly applicable to beads coated with other MHC molecules such as MHC Class II HLA molecules and non-classical MHC molecules.

Another embodiment of the invention is directed to the in vivo administration of peptides, peptides associated with MHC molecules, and/or peptides associated with MHC molecules covalently attached to beads, to patients. Based on these ex vivo and in vitro applications, there is also a separate set of clinical translational applications whereby these MHC+peptide complexed to beads and/or nanoparticles would be utilized in in vivo clinical applications for the treatment and/or modulation of disease conditions. First, there is the attachment of the complexes to spherical bead structures made from clinically friendly material such as available compounds for the synthesis of sutures (e.g. inert materials). Nanoparticles made from this and similar materials may be porous in nature and may therefore also be carriers of biologically stimulatory agents such as, for example, adjuvants, cytokines, CpG, pharmaceutical agents, cytotoxic drugs, DNA, RNA, etc, or biologically toxic materials. Therefore, by attaching MHC+peptide complexes of the invention to these structures, one can target the expansion or destruction of antigen-specific cells for stimulating an immune response (for cancer, infectious diseases, etc), or for inhibiting an immune response (autoimmunity, inflammatory conditions, prevent rejection of organ transplant etc.). Peptides of the invention are used in vivo for shutting down and/or modulating an unwanted or stabilizing and erratic immune response. Second, nanoparticle structures currently in clinical trials are made from lipid/complex lipid membranes (mostly similar to micelles) that can have MHC+peptide complexes inserted into the membrane and hollow in the middle. Again, these structures with the selected specific MHC+peptide may be used to stimulate or inhibit immune responses by targeting appropriate T cells and including biologically stimulatory or toxic molecules into the interior of these structures such as adjuvants, cytokines, CpG, cytotoxic drugs, DNA, RNA, etc. For example, therapeutically- or prophylactically-effective amounts of peptide of the invention, complexed with MHC molecules and, if desired, covalently attached to beads, may be administered for stimulating or inhibiting the immune response of a patient. Administration may be by injection directly into the bloodstream or other body area such as the gut, parenterally, intramuscularly, or intratumorally where possible or desirable, or to the lymph nodes or the inflammation location, or priming or pretreating the transplant organ. When administered with beads, it is also possible to localize the region of the body to which the beads migrate, and thereby have the local effect maximized, with magnetic beads or beads which respond to lines of force, or simply are attracted to certain materials, which may be introduced for that purpose or otherwise, or naturally occurring in the body.

Another embodiment of the invention is directed to nucleic acids that encode peptides of the invention. Nucleic acids may comprise DNA, RNA or PNA molecules, and encode additional sequences of use in the manipulation of the nucleic acid molecule or in the expression of encoded peptides.

Another embodiment of the invention is directed to antibodies, which respond to peptides of the invention. Antibodies may be monoclonal or polyclonal, and may also be useful in in vivo applications in a similar fashion to beads.

The following examples illustrate embodiments of the invention, but should not be viewed as limiting the scope of the invention.

EXAMPLES

The approach of using a particular or given set of these beads for basic studies or monitoring responses in the manner described above whereby they are used as a panel or array of bead combinations containing various specific peptides (e.g. infectious disease antigens or cancer-associated antigens) and to include the control peptides would also be a novel application of our discovery. The screening of blood samples and cultures for responses to a specifically defined panel of beads is not only useful in the monitoring of immune responses in evaluating and diagnosing healthy or diseased conditions, but also for the purposes of discovery of new customized antigenic epitopes from proteins. Examples of these include the study of epitope-spreading in cancer vaccination, study of enhancement and broadening of immune responses to vaccination regimens and adjuvants, and various delivery systems and discovery of potentially new vaccine peptides from tumor antigens and infectious organisms.

The stimulation of peripheral blood cell populations and in vitro-stimulated cultures for the elicitation of functional activities such as cytokine secretion (ELISA and ELISPOT), proliferation and cytotoxicity activity are measured by standard and novel immunological assays (including flow cytometry and/or radioactivity measurements and/or colormetric measurements, etc.).

These measurements are utilized for understanding and evaluating immune responses such as the monitoring of clinical trials and basic research investigations. Immunological monitoring of clinical trials and basic research investigations also include the investigation/elucidation of signal transduction pathways and related components and calcium mobilization studies in immune cells from both healthy and disease conditions (see U.S. Pat. No. 5,550,214).

In another embodiment, beads (such as those commercially available from DYNAL) are covalently coupled to MHC Class II HLA molecules. The MHC Class II HLA-coated beads are incubated to a cell population for a period of time; quantitating proliferation of the cell population. A test bead was incubated with a test cell population for a period of time, wherein the test bead was covalently attached with a test MHC molecule; quantitating proliferation of the test cell population. The proliferation of the cell population is subtracted from the test population to quantitate proliferation caused by said test peptide. The stimulation of peripheral blood cell populations and in vitro-stimulated cultures for the elicitation of functional activities such as cytokine secretion (ELISA and ELISPOT), proliferation and cytotoxicity activity are measured by standard and novel immunological assays (including flow cytometry and/or radioactivity measurements etc.). These measurements are utilized for understanding and evaluating immune responses such as the monitoring of clinical trials and basic research investigations. Immunological monitoring of clinical trials and basic research investigations also include the investigation/elucidation of signal transduction pathways and related components and calcium mobilization studies in immune cells form both healthy and disease conditions.

In another embodiment, experiments were conducted with the E75 or Telomerase peptides+HLA beads in ex vivo ELISPOT assays run in the absence of stimulation (i.e. culture medium) or with plain or non-complexed E75 or Telomerase peptides. Test results showed that these DYNAL beads+

HLA+peptides were capable of eliciting good clean results in the ELISPOT assay for the detection of IFN-gamma-secreting cells. These responses have been reproduced in a number of assays using peripheral blood samples from prostate and breast cancer patients. The beads need not be made by DYNAL Biotech. Another biochemical manufacturer—such as BD Biosciences, may produce them.

In another embodiment, experiments were conducted with the E75 or Telomerase peptides+HLA beads in ex vivo ELISPOT assays run with negative control peptides. These results demonstrated that good, clean quantitation of IFN-gamma-secreting cells can be obtained or measured in this manner, or measured using this system and approach (see Table I).

To perform such studies with scientific merit, appropriate 'negative-controls' i.e. beads with HLA molecules non-covalently associated with negative control peptides and 'positive-controls' i.e. beads with known positive control peptides have to be designed, made and utilized. This provides a standard set of reagents that can be quality-controlled for the stimulation of blood cell populations and cell cultures for obtaining consistent results in immunological assays as opposed to using peptide-pulsed cell populations as antigen presenting cells which are hard to obtain and prepare and can be very variable from time point to time point. The ability of the present invention to do this in an ex vivo situation is an additional novel feature of using these beads in this way (i.e. for ex vivo monitoring of immune responses directly in cells isolated or prepared from peripheral blood).

The ideal peptide for presentation to a T cell (to elicit an immune response, an antigen must be presented and recognized by a T lymphocyte) in association with an MHC antigen for eliciting a stable, non-zero background response in an ELISPOT assay, would be a sequence of about 8-10 amino acids that are numbered starting from the amino N-terminus. The sequence contains at least two anchor amino acids, at least one of which is located at position 1, 2 or 3, and at least one other of which is located at position 7, 8 or 9. A stable non-zero background response is desirable to know there is a response elicited, yet it does not interfere with the results of the variable immune-response stimulation.

In another embodiment, the present invention provides two/three such peptides that can potentially be used as a negative control peptide for these assays-{E37 from folate-binding protein (FBP): aa 25-33) NH2-RIAWARTEL-COOH} (SEQ ID NO 1), {E39 from folate-binding protein (FBP): aa 191-199) NH2-EIWTHSTKV-COOH} (SEQ ID NO 2) wild type is EIWTHSYKV (SEQ ID NO 3). {Tert540 from telomerase: aa 540-548) NH2-I/LILAKFLHWL-COOH} (SEQ ID NO 4) wild type is EILAKFLHWL (SEQ ID NO 5). The beads and processes can also be used in conjunction with murine research by coating beads with MHC Class I H-2 molecules instead of HLA molecules, and in non-human primate research using MAMU-MHC molecules.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the following claims.

TABLE 1

| | ARTIFICIAL APC-DYNAL Beads + [MHC + Peptide] | | | | | | | |
|---|---|---|---|---|---|---|---|---|
| PBMC | E37-ve | | Tel-ve | | EBV-1&2 | | Flu M | |
| Beads/well | $5 \times 10^5$ | $1 \times 10^5$ | $5 \times 10^5$ | $1 \times 10^5$ | $5 \times 10^5$ | $1 \times 10^5$ | $5 \times 10^5$ | $1 \times 10^5$ |
| cells/well | | | | | | | | |
| $1 \times 10^5$ | 0 | 0 | 0 | 0 | 0 | 9 | 0 | 0 |
| $2 \times 10^5$ | 3 | 6 | 6 | 4 | 4 | 3 | 1 | 5 |
| $3 \times 10^5$ | 8 | 20 | 30 | 20 | 15 | 22 | 45 | 11 |
| Specific spots | | | 22 | | 7 | | 37 | |

| Peptide | CM | E37 | Tel-ve | EBV-1 | EBV-2 | FluM |
|---|---|---|---|---|---|---|
| cells/well | | | | | | |
| $3 \times 10^5$ | 2 | 1 | 8 | 8 | 23 | 25 |
| Specific spots | | 7 | 7 | | 22 | 24 |

The invention claimed is:

1. A bead to which a major histocompatibility complex ("MHC") molecule is covalently or non-covalently coupled, wherein a peptide is associated with said MHC molecule for presentation to a T cell, and wherein said peptide comprises at least two anchor residues, wherein the at least two anchor residues are located at positions 1, 2, or 3 and 8, 9, or 10, and wherein the peptide has the amino acid sequence of SEQ ID NO:4.

2. The bead of claim 1, wherein the bead is selected from the group consisting of sepharose beads, agarose beads, magnetic beads, and nanoparticles.

3. The bead of claim 1, wherein the MHC molecule is a class I MHC molecule, a class II MHC molecule, or a non-classical MHC molecule.

4. The bead of claim 3, wherein the MHC molecule is a class I MHC molecule.

5. The bead of claim 1, wherein the MHC molecule is a human leukocyte antigen ("HLA").

6. The bead of claim 1, wherein the MHC molecule is an H-2 molecule.

7. A kit comprising a plurality of the beads of claim 1.

8. The kit of claim 7, further comprising a test peptide that is non-covalently associated with a second MHC molecule, wherein said second MHC molecule is covalently attached to said bead.

9. A method of forming the bead of claim 1 comprising, in any order:
covalently attaching the MHC molecule to said bead; and
non-covalently associating said peptide to said MHC molecule.

10. A quantitative method for determining a stable, non-zero background for proliferation of a cell population from an immune response, comprising:
   incubating the bead of claim 1 with the cell population for a period of time; and
   quantitating the amount of proliferation of said cell population, wherein the amount of proliferation of said cell population comprises the stable, non-zero background.

11. The method of claim 10, wherein the amount of proliferation of said cell population is quantitated using an enzyme-linked immunosorbent spot ("ELISPOT") assay.

12. The method of claim 10, wherein the amount of proliferation of said cell population is quantitated using an enzyme-linked immunosorbent assay ("ELISA").

13. The method of claim 10, wherein the MHC molecule is a class I MHC molecule, a class II MHC molecule, or a non-classical MHC molecule.

14. The method of claim 13, wherein the MHC molecule is a class I MHC molecule.

15. The method of claim 10, wherein the MHC molecule is a human leukocyte antigen ("HLA").

16. The method of claim 10, wherein the MHC molecule is an H-2 molecule.

17. The method of claim 10, wherein the cell population comprises T cells.

18. The method of claim 10, wherein the cell population is a peripheral blood cell population.

19. The method of claim 10, wherein the amount of proliferation of said cell population is quantitated using flow cytometry or radioactivity.

20. The method of claim 10, further comprising a step of subtracting the amount of proliferation of said cell population from the amount of proliferation of a test cell population that has been incubated with a test peptide to quantitiate the amount of proliferation induced by said test peptide.

* * * * *